US000001018H

United States Statutory Invention Registration [19]

[11] Reg. Number: H1018

Hantke et al.

[43] Published: Jan. 7, 1992

[54] IMMUNOLOGICAL METHOD FOR THE DETERMINATION OF FREE SUBSTANCES HAVING HAPTEN PROPERTIES

[75] Inventors: Uwe Hantke; Rudy Thoma; Hartmut Rokos, all of Berlin; André Gadow, Bad Homburg, all of Fed. Rep. of Germany

[73] Assignee: Henning Berlin GmbH Chemie- und Pharmawerk, Berlin, Fed. Rep. of Germany

[21] Appl. No.: 232,251

[22] Filed: Aug. 15, 1988

[30] Foreign Application Priority Data

Aug. 14, 1987 [DE] Fed. Rep. of Germany ..... 3727238

[51] Int. Cl.[5] ..... G01N 33/552; G01N 33/545; G01N 33/78

[52] U.S. Cl. ..... 436/500; 436/527; 436/531; 436/817

[58] Field of Search ..... 436/500, 518, 527, 532, 436/537, 542, 815

[56] References Cited

U.S. PATENT DOCUMENTS 4,410,633 10/1983 Hertl et al. ..... 436/500
4,434,236 2/1984 Freytag .

FOREIGN PATENT DOCUMENTS 561056 4/1987 Austria .
0089806 9/1983 European Pat. Off. .
0143274 6/1985 European Pat. Off. .
0155104 9/1985 European Pat. Off. ..... 436/500
8303306 9/1983 World Int. Prop. O. .
8500226 1/1985 World Int. Prop. O. ..... 436/500

*Primary Examiner*—John S. Maples
*Assistant Examiner*—Joseph D. Anthony
*Attorney, Agent, or Firm*—Cushman, Darby & Cushman

[57] ABSTRACT

1. Immunological method for the determination of free substances having hapten properties.

2.1. Immunological methods for the determination of free substances having hapten properties, especially of free thyroid hormones, are based on various determination principles, all of which either have disadvantages from the practical viewpoint or, by reason of the basic principle of the method, provide limited information in marginal cases. The new method is intended to simplify and improve the routine clinical determination of free substances, because of the avoidance of sources of error associated with known methods, while having a procedure which is straightforward for practical use.

2.2. The method for the determination of free substances which has hitherto existed only as a theoretical model, in which a labelled antibody and an excess of the substance which is to be determined and is in immobilized form are added to the sample to be investigated, becomes a reilable method for the determination of free substances when, in contrast to previous assumptions, the affinity of the immobilized substance with respect to the labelled antibody is less than 50% of the affinity of this antibody with respect to the substance which is to be determined in the sample.

2.3. Routine clinical determination of free substances, especially thyroid hormones.

10 Claims, 1 Drawing Sheet

Figure 1:
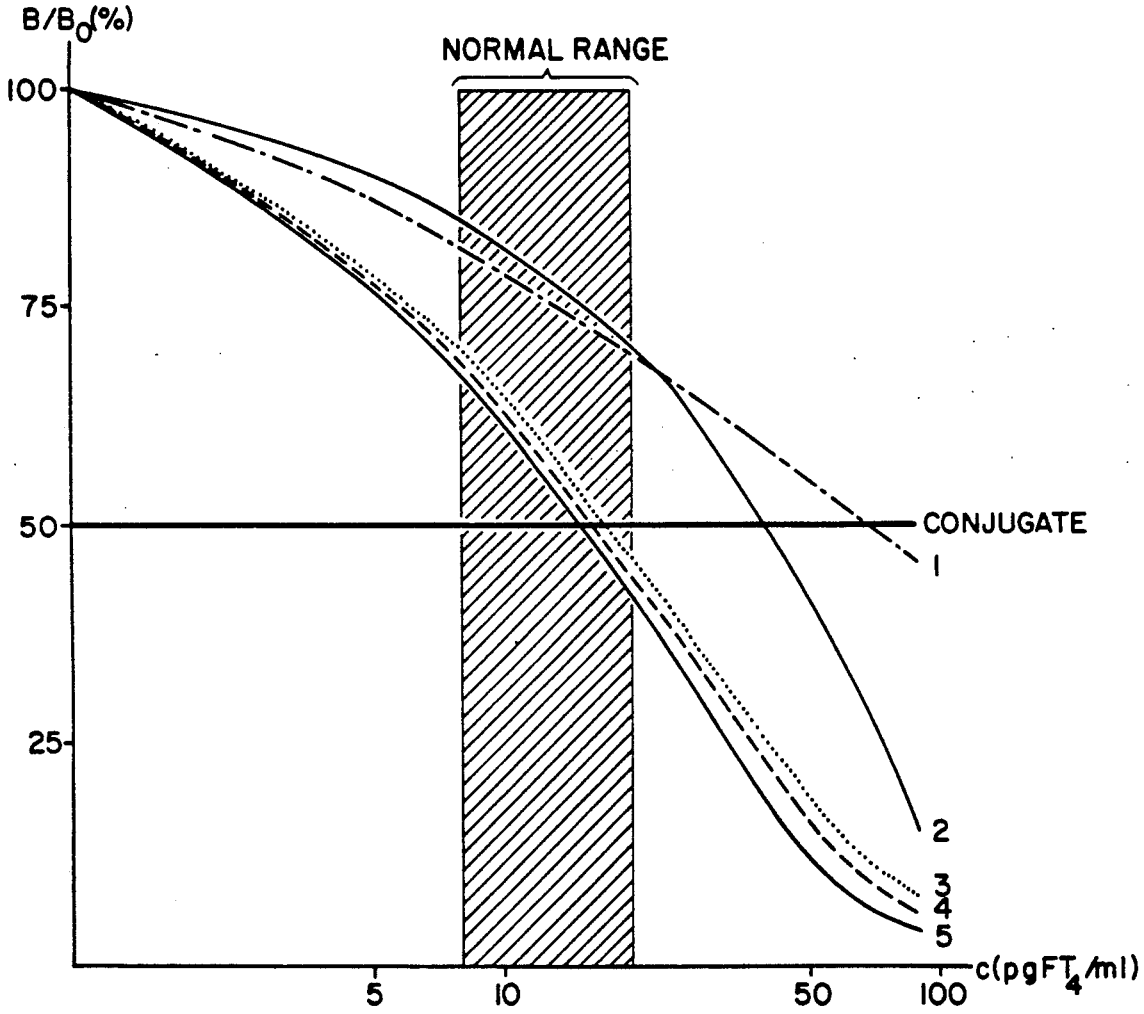

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

IMMUNOLOGICAL METHOD FOR THE DETERMINATION OF FREE SUBSTANCES HAVING HAPTEN PROPERTIES

The invention relates to an immunological method for the determination of free substances having hapten properties, especially hormones, steroids, drugs or metabolites thereof, vitamins or toxins, in biological fluids in the presence of one or more physiological binding partners for the substances which are to be determined. In this connection, the total quantity of substances of this type in the biological fluid which is to be investigated is distributed over a free and a bound fraction. In this connection, the bound fraction is bound to one or more physiological binding proteins or similar binding partners for these substances which are capable of binding the particular substance more or less specifically with a defined affinity.

The bound and non-bound fractions are in mutual equilibrium, it being assumed on the basis of the theories currently valid that the non-bound fractions, that is to say the free substances, represent the physiologically active component, whereas the bound fractions form a type of reservoir for making this substance available. In addition, there is also known to be binding of particular substances to so-called transport proteins which act to distribute the substances in the organism and transport them to the site of action.

It has become the general conviction in recent years that the determination of the free substances, that is to say the physiologically active fractions of a substance, is of more value in clinical diagnosis than is the simultaneous determination of bound and non-bound fractions. An article by R. P. Ekins entitled "The direct immunoassay of free (non-protein bound) hormones in body fluids" in: Immunoassays For Clinical Chemistry, edited by W. N. Hunter and J. E. T. Corrie, Churchill Livingstone, 2nd edition (1983), pages 319 to 339 explains the reasons for a determination of the free substances on the basis of model hypotheses. Moreover, an attempt is made to list various types of immunological determination methods which might be suitable for a determination of free substances.

European Patents 26,103 and 73,865, as well as German Patent 3,415,818, describe immunological determination methods for free substances which have been developed to the stage of practical applicability.

Since it is particularly important medically to establish the physiological status of the thyroid via determination of the free thyroid hormones L-thyroxine ($T_4$) and L-triiodothyronine ($T_3$), said patents primarily relate to determination methods of this type and discuss the application of the basic methods described to this specific case. The primary importance of the immunological determination method described in the present application also lies in establishing the physiological status of the thyroid.

The binding proteins, over which the $T_4$ circulating in the living human organism is distributed, are albumin (about 10%), thyroxine-binding prealbumin (TBPA, about 30%) and thyroxine-binding globulin (TBG, about 60%). Only 0.01 to 0.03% is in the form of physiologically active free $T_4$ ($FT_4$). This means that the normal range of concentration of $FT_4$ is from about 8 to 20 pg/ml of body fluid.

The recognized reference method for the determination of $FT_4$ is at present the equilibrium dialysis of serum (compare Clin. Invest. 45 (1966), pages 153 to 163). This entails radioactive $T_4$ being added to the serum, or the $T_4$ content in the dialysate being found directly in a $T_4$ radioimmunoassay. However, despite its high reliability, this method is unsuitable for routine clinical diagnosis because of the unacceptably long time needed for each determination, approximately 20 h.

Hence, besides methods which have a more indicative character and in some cases give rise to considerable inaccuracies, there have been developed for routine clinical diagnosis, immunological determination methods which can give direct information about the concentration of the free substances which are to be determined. In this connection, the immunological determination methods of this type which have hitherto been developed to the stage of practical application and which are, in particular, radioimmunoassays, operate on the known competition principle in which a labelled form of the substance which is to be determined is added to the sample which is to be investigated, and subsequently, after reaction with a suitable antibody, conclusions are drawn about the concentration of the substance which is to be determined from the fraction of the bound form established on the basis of the antibody labelling. In this connection, in order to rule out interference due to variations in the binding proteins in a determination of free substances, especially of $FT_4$, in the known methods so-called $T_4$-analogue tracers are used as labelled forms of the substance which is to be determined ($FT_4$). These tracers, have by reason of their chemical structure, a distinctly reduced affinity for the binding proteins and thus are said to have a minimal effect on the free substance/bound substance equilibrium. However, various authors have cast doubt on the clinical value and validity of these methods, at least for certain specific cases (Helenius, T., Liewendahl, K., Clin. Chem. 29(5) (1983), pages 816–822 Mardell, R., Gamlen, T. R., The Lancet, 24th Apri pages 973 to 974; Gow, S. M. et al., Clinica Chimica Acta 152 (1985), pages 325–333; Chopra, I. J. et al., J. Clin. Endocrin. Met. 51(1) (1980), pages 135–143 and Herrmann, J. et al., Nucl.-Med. 21(5) (1982), 186–191). The methods usually fail in cases of severe illness (NTI=non-thyroidal illness) because of the large number of interfering and influencing factors (catabolites, protein loss, or fatty acids released endogenously or under the influence of heparin) (compare Reiners, Ch , Ärztl. Lab. 31 (1985), pages 331–344). Also to be in the analogue tracer methods is the enzyme immunoassay for the determination of $FT_4$ which is described by Ito, M. et al. in Clin. Chem. 30(10) (1984), pages 1682 to 1685, and in which a $T_4$-$\beta$-D-galactosidase conjugate is used as tracer and is said not to bind to the binding proteins.

An enzyme immunoassay described by Weetall et al. in Clin. Chem. 28(4) (1982), pages 666–671, is based on the distribution of a $T_4$-horseradish peroxidase conjugate to the free and protein-bound fractions and a complex mathematical model for calculating the $FT_4$ fraction. The two last-mentioned methods have not as yet become part of routine clinical diagnosis.

In all the methods described hitherto, labelled forms of the substances which are to be determined, that is to say labelled antigens, have been used.

However, the use of labelled antibodies for the quantitative detection of antigens binding to these antibodies has likewise already been described in principle, specifically by Miles, L. E. M. and Hales, C. N., for the first time, in: Nature 219, (1968), pages 186–189. There is a description of a possible immunological determination of smaller molecules such as steroid hormones by use of antigen coupled to solid phases and labelled antibodies in Stafford, J. E. H. and Kilgallon, W. in: J. Immunol. Methods 34 (1980), pages 339–343, with use of a radioactive label. A similar determination using a luminescence label is described by Wood, W. G. et al. in: J. Clin. Chem. Clin. Biochem. 20(1982), pages 825–831.

In the theoretical study of Ekins which has already been quoted in the introduction there is a discussion, on page 330 with reference to the scheme described in FIG. 8.1.J, of another possible way of designing an immunological method for the determination of free substances having hapten properties in biological fluids in the presence of one or more physiological binding proteins for the substances which are to be determined. In this method, the biological fluid is reacted with a defined quantity of a specific antibody against the substance which is to be determined, or of an antibody mixture, with a detectable tracer portion and, furthermore, with an excess of the substance which is to be determined, or of a derivative of this substance, in a form immobilized by binding to a solid phase, with the solid phase subsequently being separated from the liquid phase, and the content of labelled antibody in the liquid and/or solid phase being established by measuring the label, and then the content of the free substances which are to be determined in the biological sample being found by computational evaluation of the results of measurement obtained. It is assumed, in order for the considerations on which this method is based to be valid, that the properties of the antigen bound to the solid phase are such that there is 100% cross-reactivity with the labelled antibody, or antibody mixture, which is used compared with the antigen present in the free form. Thus, the labelled antibody ought to have comparably high binding affinities to the free antigen and to the antigen bound to the solid phase in order for a determination by this method to be possible. However, successful development in practice of a determination method of this type has not as yet been reported.

German Offenlegungsschrift 3,442,817 describes a modification of the principle of the method, which has just been described, for the quantitative determination of $FT_4$, in which the sample is first incubated for not more than 10 min and in a 10- to 2000-fold excess, based on the total molar quantity of $T_4$, with a labelled anti-$T_4$ antibody. Immediately thereafter excess immobilized $T_4$ is added, and renewed incubation is carried out for at least 1 min. The phases are then separated, and the label in one of the phases is measured. This method of German Offenlegungsschrift 3,442,817 is a typical "kinetic" method which is evidently based on the assumption that, during the first brief incubation with the labelled anti-$T_4$ antibody, initially only the quantities of $T_4$ which are present in the free form are captured, with there being no release, due to slow return to equilibrium, of previously bound $T_4$, which would falsify the results of measurement. Since the duration of the preincubation may affect the result of the assay due to the known rapid attainment of equilibrium between free $T_4$ and bound $T_4$, this assay ought, like all similar two-stage assays, to have the disadvantage that it is prone to interference from changes in the assay conditions, which makes it difficult to use the relevant method in clinical practice.

The object of this invention is to provide a method for the determination of free substances which is suitable for routine clinical diagnosis, is straightforward to carry out is relevant in terms of the clinical information, yielded has optimal sensitivity and furthermore allows a manufacturer to carry out optimal quality control of the materials and substances required for the determination method.

This object is achieved by the use of an immunological determination method according to the preamble of Patent claim 1 according to the features to be found in its characterizing part.

Advantageous embodiments are to be found in the subclaims. The present invention is based on the surprising recognition that, for the development of an immunological determination method based on a basic method which is known per se, as has been described by, for example, Ekins (loc. cit.), it is necessary for the antigens bound to the solid phase to have a greatly reduced cross-reactivity of distinctly less than 50%, preferably in the range from 8 to 25%, compared with the free antigen which is to be determined, if a determination method which has sufficiently high sensitivity and reproducibility for practical purposes is to be obtained. It has emerged, surprisingly, that higher cross-reactivities, in the region of or above the 100% cross-reactivity proposed by Ekins (loc. cit.), lead to distinctly falsified results, and that the measurement range is then outside the clinically relevant concentration range for the free substance. It has also emerged that when the cross-reactivities are maintained within the stated range, the preincubation necessary in the method of German Offenlegungsschrift 3,442,817 is superfluous, and the method can be carried out in one stage since the biological fluid can be reacted essentially simultaneously with the labelled antibody and the immobilized antigen which is present in excess.

This possibility of a one-stage procedure represents a considerable advantage. Owing to the choice of suitable antibodies or antibody mixtures of defined affinity, in the one-stage procedure there is no, or only inconsiderable, intervention in the free substance/bound substance equilibrium, so that the different cross-reactivities of the free substance and of the immobilized substance with the labelled antibody mean that it is necessary to take account only of the kinetics of binding of the labelled antibody to the immobilized antigen. However, where the incubation times vary, this has an effect on the binding ratios and not on a displacement of the free substance/bound substance equilibrium.

Thus, it is preferable to carry out the method according to the invention as a one-stage method without preincubation, which means a considerable simplification.

Although the method according to the invention should be suitable generally for the determination of free substances having hapten properties, especially of hormones, steroids, drugs or metabolites thereof, vitamins or toxins, in biological fluids, it is particularly important in connection with the determination of $FT_4$ and $FT_3$.

Furthermore, the method according to the invention has all the known advantages of determination methods using a reactant immobilized by binding to a solid phase. The immobilization on a solid phase markedly simplifies the washing steps which are necessary, and the precision of the determination is improved. Suitable solid phases to which is bound the immobilized form of the substance which is to be determined are all inert carrier materials which are known per se and which have sufficiently stable binding properties and an adequately high binding capacity, which include plastics such as polystyrene, polyethylene and Teflon, Suitable solid phases are also described in U.S. Pat. No. 657,873 and in a publication by Wood, W. G. and Gadow, A. in: J. Clin. Chem. Clin. Biochem. 21 (1983), pages 789–797. The antibodies used are labelled by known methods using detectable tracer portions suitable for labelling. Labelling with relatively small markers which have relatively little effect on the reactivity of the antibodies is preferred within the scope of the present invention. These are, in particular, radioisotopes, especially iodine isotopes, and luminogens. However, assuming that the tracer portions allow the required cross-reactivities with respect to a suitable antibody to be maintained, also suitable as markers are, for example, enzymes, substrates, fluorescent labels, phosphorescent labels, biotin (detectable via labelled avidin) or cofactors. It is also possible to use indirect labelling methods in which the marker is detached again from the antibody before the measurement, as well as all substances which can be detected quantitatively on the basis of an optical, physical or chemical reaction.

Suitable antibodies for the method according to the invention are all antibodies known to be suitable for methods of this type. Antibodies of this type preferably have an affinity for $T_4$ and $T_3$ which is no greater than the respective affinity of $T_4$ and $T_3$ for the physiological binding proteins. Anti-$T_4$ (or $T_3$) anti-bodies of this type normally have an affinity constant of $10^{10}$ l/mol or less.

In the method according to the invention, the immobilized substance or its derivative is preferably immobilized on the solid phase in the form of a conjugate with a carrier substance. Suitable carrier components for this are high molecular weight substances such as proteins, polypeptides or polysaccharides, towards which the labelled antibody and the labelled antibody mixture have a cross-reactivity of less than 0.5%. Suitable and preferred carrier components are those which are not identical to the carrier component to which the substance to be determined was bound for the production of the antibodies used.

In this connection, it has emerged that the cross-reactivities of a particular conjugate may vary widely even if it has been prepared from identical starting materials under identical conditions. Apparently identical conjugates, especially in immobilized form, may thus display very different cross-reactivities. Hence the cross-reactivities of each particular batch with respect to the antibody used must be determined in order to determine suitability for the method according to the invention. The determination of the cross-reactivity then permits a definite statement to be made about the possibility of using the relevant conjugate in the method according to the invention. These circumstances differ markedly from the circumstances existing in the case of direct use of the substance which is to be determined, or a derivative thereof, in immobilized form or in solution, where the cross-reactivity with respect to a particular antibody depends only on the nature of the substance itself.

The incubation conditions for carrying out the method according to the invention depend, within certain limits, on the particular antibodies used, including consideration of the effects on their binding properties by the label used, and on the exact cross-reactivities within the range established by the present invention. Suitable incubation conditions comprise incubation temperature of 17° to 37° C. and incubation times of 30 min to 3 h. Preferred incubation conditions are the incubation conditions used in the example, which provide for incubation at 22° C. for two hours (±10 min), with shaking, preferably in a horizontal shaker.

The significance of the reduced cross-reactivity of the substance, or derivative thereof, which is bound to the solid phase with respect to the quality of the resulting assay method is explained in detail hereinafter with the aid of examples which relates to the determination of $FT_3$ and $FT_4$, preferred within the scope of the present invention.

Preparation of $T_4$ derivatives used for the immobilization

1. L-Thyroxine ethyl ester (L-$T_4$ OEt)

Thyroxine ethyl ester was prepared by the modified method of Clayton, J. C. and Hems, B. A., J. Org. Chem., 1950, pp. 840–843.

2. N-Trifluoroacetylthyroxine ($TFAT_4$)

The title compound was prepared by the modified method of Schroeder et al. in: Methods in Enzymology, Vol. 57, Bioluminescence and Chemiluminescence, New York, Academic Press 1978, pages 424–445.

For this purpose, 5 g of L-thyroxine were dissolved in 60 ml of absolute ethyl acetate, and 11.5 ml of trifluoracetic acid and 1.9 ml of trifluoroacetic anhydride were added. The mixture was stirred at 0° C. for 1 h.

The reaction mixture was then allowed to warm to room temperature. 200 ml of water were added to the reaction mixture, and the resulting solution was saturated with sodium chloride. The organic phase was separated off, washed with a saturated sodium chloride solution and dried over dry magnesium sulphate. The dried phase was filtered and evaporated to dryness. The pure residue was used without further purification for the subsequent syntheses.

Yield: 4.8 g.

Analytical data: elemental analysis: Calculated: C 23.39%, H 1.15%, N 1.60% Found: 23.19% 1.12% 1.63%.

Preparation of conjugates of $T_4$ or of $T_4$ derivatives

Conjugate 1: IgG-L-$T_4$OEt conjugate (coupling at $NH_2$)

The conjugate was prepared by the active ester method.

80.5 mg of L-$T_4$OEt and 11 mg of succinic anhydride were dissolved in 2 ml of dry and amine-free DMF and stirred at room temperature overnight. Then 12.6 mg of N-hydroxysuccinimide and 22.6 mg of N,N'-dicyclohexylcarbodiimide were added to the reaction mixture, and it was stirred at room temperature for 1 h.

The active ester mixture was used without further purification for preparing the conjugate.

For this purpose, 100 mg of rabbit IgG (SIGMA, Munich) were dissolved in 20 ml of water. 200 μl of the active ester were diluted in 800 μl of dry and amine-free DMF and added to the aqueous solution of rabbit IgG. After about 12 h, the reaction mixture was purified by ultrafiltration.

Yield: 85 mg.

The L-$T_4$OEt incorporation rate determined by UV spectroscopy was 4.2 per mole of IgG.

Structure of the conjugate

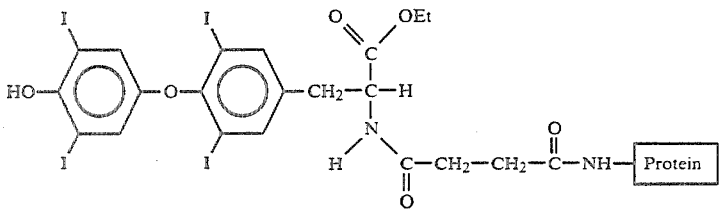

Conjugate 2: IgG-L-$T_4$ conjugate (coupling at $NH_2$ and COOH)

The conjugate was prepared by the carbodiimide method.

1 g of rabbit IgG (SIGMA, Munich) was dissolved in 100 ml of double-distilled water and equilibrated at 10° to 15° C.

200 mg of L-thyroxine (Henning Berlin, Berlin) were dissolved in 5 ml of an alkaline 1:1 mixture of dry, amine-free DMF and methanol.

1.25 ml of the thyroxine solution and 100 mg of solid 1-ethyl-2-(3-dimethylaminopropyl)carbodiimide (EDC) were added at intervals of 1.5 hours to the stirred aqueous IgG solution, and the pH was maintained between 5 and 6. After the last addition, the mixture was left at 4° C. overnight and then purified by ultrafiltration.

Yield: 860 mg.

The L-$T_4$ incorporation rate determined by UV spectroscopy was 4.3 per mole of IgG.

Structure of the conjugate

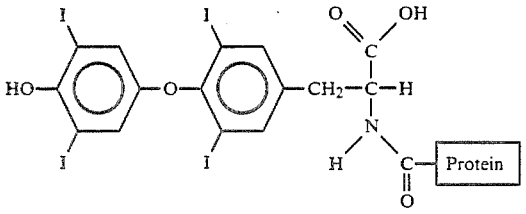

or

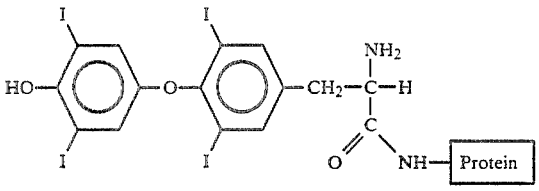

Conjugate 3: IgG-L-$T_4$ conjugate (coupling at COOH)

The conjugate was prepared by the carbodiimide method.

43.6 mg of N-trifluoroacetylthyroxine, 6.32 mg of N-hydroxysuccinimide and 11.33 mg of N,N'-dicyclohexylcarbodiimide were dissolved in 1 ml of dry, amine-free DMF and stirred at room temperature for 1 h.

100 mg of rabbit IgG (SIGMA, Munich) were dissolved in 20 ml of double-distilled water.

400 μl of the active ester mixture were diluted with 600 μl of dry and amine-free DMF and added to the aqueous IgG solution. After the reaction mixture had been stirred at room temperature for about 12 hours, it was purified under ammoniacal conditions by ultrafiltration, there being simultaneous elimination of the trifluoroacetyl protective group.

Yield: 94 mg.

The L-$T_4$ incorporation rate determined by UV spectroscopy was 11.5 per mole of IgG.

Structure of the conjugate

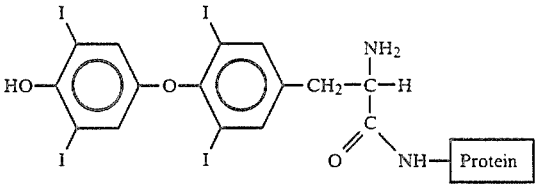

Conjugate 4: IgG-L-$T_4$OEt conjugate (coupling at $NH_2$)

The conjugate was prepared by the carbodiimide method.

10 g of rabbit IgG (SIGMA, Munich) were dissolved in 1000 ml of double-distilled water.

1.25 g of L-$T_4$OEt were dissolved in 40 ml of methanol (slightly acidic) and added, together with 2.5 g of EDC to the aqueous IgG solution. The reaction mixture was stirred at room temperature and constant pH of about 5 with exclusion of light for 2 hours and then stored at 4° C. overnight. The mixture was then purified by ultrafiltration.

Yield: 6.8 g.

The L-$T_4$OEt incorporation rate determined by UV spectroscopy was 1.5 per mole of IgG.

Structure of the conjugate

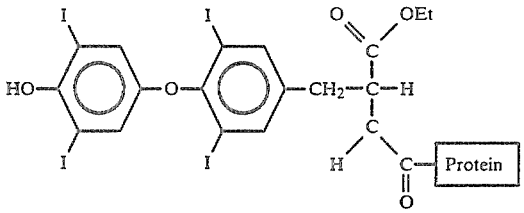

Conjugate 5: L-$T_4$-IgG conjugate (coupling at $NH_2$ and COOH)

The conjugate was prepared by the carbodiimide method.

500 mg of L-thyroxine (Henning Berlin, Berlin) were dissolved under weakly alkaline conditions in 500 ml of double-distilled water containing 10% dry and amine-free DMF.

5 g of rabbit IgG were dissolved in 500 ml of double-distilled water. The two aqueous solutions of L-thyroxine and rabbit IgG were mixed and, while stirring, a total of 1.9 g of EDC were added in 10 portions at intervals of about 10 min. The reaction mixture was subsequently left to stand at 4° C. overnight and then purified by ultrafiltration.

Yield: 2.3 g.

The L-$T_4$ incorporation rate determined by UV spectroscopy was 3.3 per mole of IgG.

The structure of the resulting conjugate corresponded to the structure depicted for conjugate 2.

Determination of the cross-reactivities of the prepared conjugates with respect to antibodies General method: For carrying out the cross-reactivity tests, the poly- or monoclonal antibodies, or mixtures of these antibodies, which were used were covalently bonded to microparticles which contained epoxy groups and had a uniform particle size of 1.055±0.032 μm. The amount the antibodies/antibody mixtures coupled in each case was 350 μg of purified antibodies or antibody mixture per gramme of microparticles. Any further binding sites present after the coupling were saturated with inert substances. The microparticles prepared in this way were taken up in 10 ml of 0.1M phosphate buffer, including 1 mol/l NaCl and 0.05% azide, pH 7.2, per gramme of microparticles.

The tracer used for the cross-reactivity tests was $^{125}$I-labelled thyroxine with a specific activity of 6.22 MBq/μg in a concentration of 27.6 mg/l.

The conjugates to be investigated, as well as the thyroxinge (or triiodothyronine) used as reference substance (substance to be determined), were made up fresh, for each assay procedure, in a buffer matrix composed of 20 mmol/l phosphate buffer containing 0.2% gelatin and free of binding proteins. The following concentrations were chosen for this: $FT_4$: 7.8, 16, 31, 62, 125, 250 and 500 ng L-$T_4$/ml The concentrations of the conjugates were adjusted as follows: Conjugates: 0.01, 0.1, 1, 10 and 100 μg of conjugate/ml.

The scheme used for the mixtures for all the cross-reactivity tests was the following:

100 μl of buffer (0 standard) or standard
+100 μl of $^{125}$I-labelled thyroxine (tracer)
+1 ml of microparticle suspension of a suitable dilution.

The dilution of the microparticle suspension coupled to the antibodies which was to be used for this was adjusted so that the range with the greatest discrimination was found to be a range between 30 and 40 ng of $T_4$/ml.

The mixture was incubated at 22° C. for 1 h.

Centrifugation at 2000×g for 10 min, followed by aspiration of the supernatant from the microparticles which had been sedimented in the centrifugation, until they were dry (bound/free separation), and measurement of the bound phase in a gamma counter for 60 seconds, provided the results from which the cross-reactivities of each of the conjugates to be investigated were determined by known methods.

The cross-reactivities obtained using mouse antibodies are shown in the penultimate column in the table which follows.

| Conj. No. | L-$T_4$ derivative | Coupling at | Incorporation rate (mol $T_4$/mol IgG) | x-react. (%) | 50% intercept (pg/ml) |
|---|---|---|---|---|---|
| 1 | L-$T_4$OEt | $NH_2$ | 4.2 | 310 | 70 |
| 2 | L-$T_4$ | $NH_2$/COOH | 4.3 | 36 | 40 |
| 3 | L-$T_4$ | COOH | 11.5 | 28 | 17 |
| 4 | L-$T_4$OEt | $NH_2$ | 1.5 | 13.5 | 16 |
| 5 | L-$T_4$ | $NH_2$/COOH | 3.3 | 9.5 | 15 |

The last column in the table is a "50% intercept" (pg/ml) column which was determined on the basis of Examples 1 and 2 which follow. This column reveals whether a particular conjugate was suitable, in conjunction with the antibody investigated, for use in the method according to the invention. When the 50% intercept, which reflects the region of greatest slope of the standard plot, and thus the greatest discrimination between small differences in concentration, is in the normal physiological concentration range for $FT_4$ of 8 to 20 pg/ml, the corresponding conjugate is very well suited for use in the method according to the invention.

It can be seen that these conditions are met by those conjugates whose cross-reactivity is below 30% (from 9.5 to 28%). When the cross-reactivity is 36%, the 50% intercept is 40 pg/ml, which already signifies a distinct reduction in the sensitivity of the assay.

The figures given in the last column of the table above, which were determined under identical assay conditions (Examples 1+2), can also be seen in FIG. 1 attached.

The method according to the invention, which was also used in the described form for determining the figures shown in the last column of the Table and the plots depicted in FIG. 1, is also described in more detail hereinafter on the basis of two concrete examples:

EXAMPLE 1

Method for determining free thyroxine ($FT_4$)

1 μg of each of the conjugates to be investigated was coupled to the solid phase which, in the present example, was a coated polystyrene tube known per se.

The antibody used was a monoclonal $T_4$-specific mouse antibody. The antibody was labelled with $^{125}$I in a known manner. The specific activity of the resulting labelled antibody was between 25 and 35 KBq/μg of antibody. The labelled antibody was taken up in 0.1 M phosphate buffer containing 1 mol/l NaCl and 0.05% azide, pH 7.2. The concentration of the labelled antibody was between 1 and 1.25 μg/l in this.

The standard material used was a human serum matrix with the following concentrations: 0, 2.8, 5.6, 11.3, 22.5, 45 and 90 pg of $FT_4$/ml.

The assay was carried out as follows:

50 μl of standard material were pipetted into the polystyrene tube containing the immobilized conjugate to be investigated, and 500 μl of $^{125}$I-labelled antibody (tracer) were added.

The reactants were incubated!at 22° C. on a horizontal shaker for 2 h. The immunological reaction was stopped by aspirating the incubation solution out of all the tubes.

4 ml portions of washing solution (0.15 mol/l NaCl) were placed in each of the tubes, followed by decantation, times.

The activity remaining bound to the solid phase was measured in a gamma counter for 60 seconds. The results obtained were evaluated by data reduction by known methods.

EXAMPLE 2

Determination of free thyroxine ($FT_4$)

Coated polystyrene tubes as in Example 1 were used for the immobilization of the conjugate to be investigated.

Once again the antibody used was a monoclonal $T_4$-specific mouse antibody, but this time it was labelled not with a radionuclide but with a luminogen. The luminogen had been coupled to the antibody in a manner known per se (compare U.S. Pat. No. 4,645,646; German Offenlegungsschrift 2,921,781 or 3,132,491). A cyclic diacylhydrazide derivative was used as luminogen.

The antibody labelled with the luminogen was taken up in 0.1M phosphate buffer containing 1 mol/l NaCl and 0.05% azide, pH 7.2. The concentration of the labelled antibody was between 1 and 1.25 μg/l in this.

The standard material used was the same human serum matrix as in Example 1. The assay procedure also corresponded exactly to that in Example 1.

The activity remaining bound to the solid phase was measured in a luminometer suitable for measuring chemiluminescence and having at least one possibility for injection in the measuring position (Berthold LB 9502 or Hamilton LUMICON) for 4 s. The measurement method and the reagents used for this are described in detail in, inter alia, the already cited U.S. Pat. No. 645,646.

Subsequent data reduction by known methods provided the concentrations which were sought.

The solid phases used in the two examples of the method, 1 and 2, were coated polystyrene tubes. However, it is possible without difficulty also to use as solid phases other plastics (for example polypropylene, nylon, Teflon and other suitable activated plastics) as well as glass. The coupling of the conjugates in these cases is always carried out by methods known from the literature, for example by adsorption or covalently (compare Catt, K., Tregear, G. W., in: Science, 158 (1967), pages 1570–1572; U.S. Pat. No. 4,657,873 or Wood W. G. and Gadow, A. in: J. Clin. Chem. Clin. Biochem. 21 (1983), pages 789–797.

In place of the labelling with radionuclides ($^{125}I$) and luminogens used in Examples 1 and 2, it is also possible to label in other ways known per se, for example, by using enzymes, substrates, fluorescers or other detectable substances, in which case suitable detection methods will of course, have to be chosen.

The experiments included in the present application all relate to the detection of $FT_4$. Results of experiments which relate in the same manner to the suitability of the method according to the invention for the determination of $FT_3$ are also available. They confirm the statements in the present description.

We claim:

1. An immunological method for the determination of unbound molecules of a substance having hapten properties, which substance is selected from the group consisting of hormones, steroids, drugs, metabolities of drugs, vitamins and toxins, in a biological fluid in the presence of one of more psychological binding partners for said substance comprising:

(i) reacting the biological fluid with (a) a defined quantity of a labelled antibody specific for said substance and (b) an amount of an immobilized form of said substance or derivative thereof, wherein said amount is higher than the approximate amount of said substance present in the biological fluid which immobilized form of said substance or derivative thereof has a reduced reactivity towards the physiological binding partners in comparison to the unbound molecules of said substance (ii) separating the solid phase from said fluid subsequent to said reaction and (iii) determining the content of said labelled antibody associated with said fluid or said solid phase whereby the quantity of unbound molecules of said substance in the fluid is established by the use of calibration plots, wherein the immobilized form of said substance or derivative thereof is selected so that the affinity of said labelled antibody for said immobilized form is less than 50% of the affinity of said labelled antibody for the unbound molecules of said substance.

2. Method according to claim 1 wherein the cross-reactivity of the selected specific labelled antibody for the immobilized form of the substance is in the range from 8 to 25% as compared to the cross-reactivity of said antibody for the unbound molecules of said substance.

3. Method according to claim 1 or 2, wherein the biological fluid containing unbound molecules of said substance is contacted with said labelled antibody and the immobilized form of the substance or derivative thereof, essentially simultaneously.

4. Method according to one of claim 1 or 2 wherein said substance, the unbound portion of molecules of which is to be determined, is L-thyroxine of L-triiodothyronine.

5. Method according to claim 1 or 2 wherein said solid phase is plastic or glass.

6. Method according to claim 1 wherein the immobilized form of the substance or derivative thereof is present in the form of a conjugate wherein said conjugate comprises the substance and antibody thereto and is bound to the solid phase via a carrier component.

7. Method according to claim 6 wherein said carrier component is a protein, polypeptide or a polysaccharide.

8. Method according to claim 6 or 7 wherein the labelled antibody has an affinity for the carrier component of less than 0.5% of the affinity of the labelled antibody for said molecules of unbound substance.

9. Method according to claim 1 wherein (a) said substance, the unbound portion of molecules of which is to be determined, is L-thyroxine or L-triiodothyronine;

(b) the cross-reactivity of the selected, specific labelled antibody is in the range from 8 to 25% and (c) the immobilized form of the substance or derivative thereof is present in the form of a conjugate bound to the solid phase via a carrier component wherein said conjugate comprises said substance and antibody thereto.

10. The method according to claim 9, wherein said antibody has an affinity for L-thyronine and L-triiodothyronine which is less than the respective affinity of L-thyronine and L-triiodothyronine for the physiological binding proteins.

* * * * *